United States Patent [19]

Beauchamp

[11] Patent Number: 5,079,252

[45] Date of Patent: Jan. 7, 1992

[54] THERAPEUTIC COMPOUNDS

[75] Inventor: Lilia M. Beauchamp, Raleigh, N.C.

[73] Assignee: Buroughs Welcome Co., Research Triangle Park, N.C.

[21] Appl. No.: 379,525

[22] Filed: Jul. 13, 1989

[30] Foreign Application Priority Data

Jul. 14, 1988 [GB] United Kingdom ............... 8816760

[51] Int. Cl.$^5$ ................. A61K 31/52; C07D 473/00
[52] U.S. Cl. ................................. 514/262; 544/276
[58] Field of Search ................. 544/276; 514/262

[56] References Cited

U.S. PATENT DOCUMENTS

| 4,146,715 | 3/1979 | Schaeffer | 544/276 |
| 4,199,574 | 4/1980 | Schaeffer | 544/276 X |
| 4,287,188 | 9/1981 | Schaeffer | 544/200 X |
| 4,294,831 | 10/1981 | Schaeffer | 544/277 X |
| 4,544,634 | 10/1985 | Krenitsky | 435/119 |
| 4,609,662 | 9/1986 | Krenitsky | 514/262 |
| 4,612,314 | 9/1986 | Verheyden et al. | 514/261 |
| 4,695,570 | 9/1987 | Krenitsky | 514/261 |
| 4,745,119 | 5/1988 | Krenitsky | 514/262 |

FOREIGN PATENT DOCUMENTS

| 20163 | 10/1983 | Australia . |
| 0145207A1 | 6/1985 | European Pat. Off. . |
| 0158513A2 | 10/1985 | European Pat. Off. . |
| 0289992A2 | 11/1988 | European Pat. Off. . |
| 1561380 | 2/1980 | United Kingdom . |

*Primary Examiner*—Cecilia Shen

[57] ABSTRACT

The present invention relates to the valeryl ester of acyclovir and pharmacologically acceptable salts thereof and their use in medical therapy particularly in the treatment of viral infections. Also provided are processes for the preparation and pharmaceutical formulations containing the compounds according to the invention.

7 Claims, No Drawings

THERAPEUTIC COMPOUNDS

The invention relates to a new ester of 9-(2-hydroxyethoxymethyl)guanine having valuable antiviral properties.

9-(2-Hydroxyethoxymethyl)guanine, otherwise known as acyclovir, possesses a potent antiviral activity, particularly against herpes viruses (H. J. Schaeffer et al, "Nature", 272 583-585 (1978), UK Patent Specification 1523865 and U.S. Pat. No. 4,199,574). Acyclovir is however poorly soluble in water, thereby limiting the formulation of the drug in aqueous pharmaceutical preparations where solubility is required.

Also acyclovir is only poorly absorbed from the gastrointestinal tract after oral administration (15% recovery in the urine when tested in rats and 20% in humans). Such low bioavailability requires the administration of large doses of drug in order to achieve and maintain effective anti-viral levels in the plasma.

United Kingdom Patent Specification 1561380 describes certain esters of acyclovir in particular $C_{2-16}$ alkyl esters having good anti-herpes activity.

We have now discovered that the valeryl ester of acyclovir, which was not specifically disclosed in either UK Patent Specification 1523865 or 1561380, surprisingly has improved bioavailability compared with either acyclovir or the esters disclosed therein. This enables less drug to be administered while still providing equivalent drug levels in the plasma after oral absorption.

According to one feature of the present invention we provide the compound of formula (I)

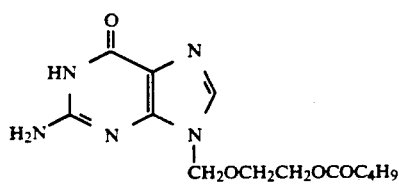

or a pharmacologically acceptable salt thereof. The compound of formula (I) can also be named as 9-(2-valeryloxyethoxymethyl)guanine.

The pharmacologically acceptable salts of the compound of formula (I) are preferably acid addition salts derived from an appropriate acid, e.g. hydrochloric, sulphuric or phosphoric acid.

Hereinafter the compounds of formula (I) and pharmacologically acceptable salts thereof will be referred to as compounds according to the invention.

In tests in rats measuring the urinary recovery as acyclovir (% dose administered) after oral administration the compounds according to the invention show an increase in absorption from the gut compared with other esters and compared with acyclovir.

In addition to the relatively high bioavailability, the compounds according to the invention possess substantially the same antiviral effect as acyclovir in vitro. The advantageous increase in bioavailability of the compounds is thus not gained at the expense of antiviral potency.

In experiments in animals it was discovered that the oral administration of the valeryl ester produced measurable levels of acyclovir in the plasma. Thus according to another aspect of the invention we provide a means of generating acyclovir in vivo by administration of the valeryl ester of acyclovir.

The present invention also provides the compounds according to the invention for use in medical therapy particularly in the treatment of a viral disease in an animal, for example a mammal such as man. The compounds are especially useful for the treatment of diseases caused by various DNA viruses, such as herpes infections, for example herpes simplex, varicella or zoster, cytomegalovirus as well as diseases caused by hepatitis B or Epstein-Barr viruses. The compounds according to the invention can also be used for the treatment of papilloma or wart virus infections. In addition to their use in human medical therapy, the compounds according to the invention can be administered to other animals for the treatment of viral diseases, for example, the active compounds are especially useful for the treatment of equine rhinophneumonitis.

The present invention also provides a method for the treatment of a viral disease in an animal, for example a mammal such as man, which comprises administering to that animal an effective antiviral amount of a compound according to the invention.

The present invention also provides the use of a compound of formula (I) in the manufacture of a medicament for the treatment of a viral infection.

Thus, according to a further feature of the present invention we provide processes for the preparation of the compound of formula (I) above and pharmacologically acceptable salts thereof which comprise:

a) reacting a compound of formula (II)

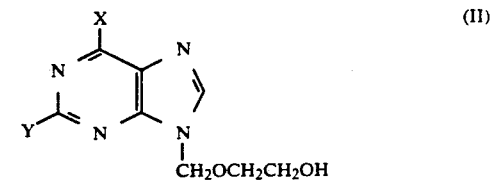

wherein X is an optionally protected hydroxy group, and Y is an optionally protected amino group with pentanoic acid or a functional equivalent thereof; or b) converting a compound of formula (III)

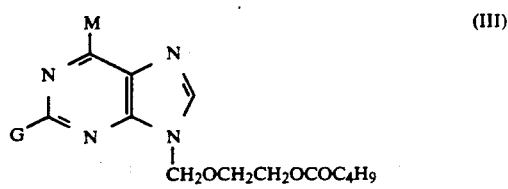

(wherein M represents a hydroxy group and G represents an atom or group that can be replaced by or converted to an amino group; or G represents an amino group and M represents an atom or group that can be replaced by or converted to a hydroxy group) into a compound of formula (I) or a pharmacologically acceptable salt thereof; or c) reacting a compound of formula (IV)

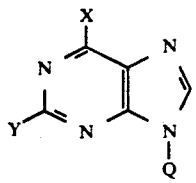

(wherein X and Y are as defined above and Q represents a leaving atom or group) with a compound of formula (V)

(wherein A represents a leaving group or atom); and optionally effecting one or more of the following conversions, in any desired sequence:

i) removal of any protecting groups;
ii) where the resulting product is a compound of formula (I), conversion of the said compound into a pharmacologically acceptable salt thereof; and
iii) where the resulting product is a pharmacologically acceptable salt of a compound of formula (I), conversion of the said salt into the parent compound.

with regard to process a), the esterification reaction may be carried out in conventional manner, for example in an organic solvent such as pyridine, dimethylformamide etc, in the presence of a coupling agent such as N,N'-dicyclohexylcarbodiimide, optionally in the presence of a catalytic base such as 4-dimethylaminopyridine. The water formed during the reaction may, if desired, be removed in conventional manner, for example by distillation or by the addition of a water-binding substance. Subsequently, the ester obtained as reaction product may be isolated in conventional manner.

As an alternative to the use of pentanoic acid per se, a functional equivalent of the acid may be employed, for example an acid halide such as the acid chloride, or an acid anhydride.

Conversion of a compound of formula (III) into a compound of formula (I), by method b), can be achieved by various means. For example G may represent an azide group which can be reduced to an amino group by catalytic hydrogenation using a suitable catalyst such as palladium on carbon. Alternatively, G may each represent a halogen atom or an alkylthio or alkylsulphonyl group which can be converted to an azide group which in turn can be converted to an amino group by catalytic hydrogenation using for example hydrogen in the presence of palladium on carbon. For the preparation of the compound of formula (I), a compound of formula (III) wherein M is an amino group may be converted to a hydroxy group for example by treatment with a deaminating enzyme such as adenosine deaminase.

These processes together with other conventional processes are described in Fused Pyrimidines, Part II, Purines, Ed. by D. J. Brown (1971), Wiley-Interscience.

In process (c), the group Q in formula (IV) may for example represent a hydrogen atom; an acyl group, e.g. a $C_{1-4}$alkanoyl group such as an acetyl group or an aroyl group such as a benzoyl group; or a tri-$C_{1-4}$alkylsilyl group such as a trimethylsilyl group. The group A in formula (V) may for example represent a halogen atom (e.g. chlorine) or an acyloxy group wherein the acyl moiety may be for example a $C_{1-4}$alkanoyl group such as acetyl or an aroyl group such as benzoyl. The reaction may be conveniently effected in a strong polar solvent such as dimethylformamide or hexamethylphosphoramide, advantageously in the presence of a base such as triethylamine or potassium carbonate. Alternatively, a thermal condensation may be effected by heating the compounds of formulae (IV) and (V) in the presence of a catalytic amount of a strong acid, for example sulphuric acid.

Compounds of formulae (II) to (VIII) employed as intermediates in the synthesis of the compound of formula (I) can be prepared in conventional manner, for example by procedures described in U.K. Patent Specification No. 1523865. These methods rely on intermediates prepared from simply substituted purines, which may be available commercially, or prepared according to techniques which are well known per se and which are disclosed in the literature such as the aforementioned text-book. Thus, for example, compounds of formula (III) may be generally prepared by using an analogous procedure to that of process (c), i.e. reacting an appropriate purine with a compound of formula (V).

The optional conversions i), ii) and iii) may be effected in conventional manner. Thus, for example, removal of protecting groups in conversion i) may be effected by hydrolysis, solvolysis or hydrogenolysis as appropriate.

With regard to protection of the groups in the 2- and/or 6-positions of purine nucleus, these may be selected for example from arylmethyl groups for example benzyl; or tri $C_{1-4}$ alkylsilyl for example trimethylsilyl. Arylmethyl blocking groups, may be removed for example by hydrogenolysis, for example by hydrogenation in the presence of Raney nickel or a palladium catalyst. Trialkylsilyl blocking groups may be removed for example by solvolysis for example by alcoholysis.

The conversion of a compound of formula (I) into a pharmacologically acceptable salt may be effected in conventional manner, for example by treatment of the compound with an appropriate acid to form an acid addition salt.

Similarly, conversion of a salt into the parent compound of formula (I) may be effected in conventional manner.

The compounds according to the invention may be administered by any route appropriate to the condition to be treated, suitable routes including oral, rectal. nasal, topical (including buccal and sublingual) vaginal and parenteral (including subcutaneous, intramuscular, intravenous, intradermal, intrathecal and epidural). It will be appreciated that the preferred route may vary with for example the condition of the recipient.

For each of the above-indicated utilities and indications, the amount required of an active ingredient namely a compound according to the invention will depend upon a number of factors including the severity of the condition to be treated and the identity of the recipient and will ultimately be at the discretion of the attendant physician or veterinarian. In general however, for each of these utilities and indications, a suitable effective dose will be in the range 0.1 to 250 mg per kilogram bodyweight of recipient per day, preferably in the range 1 to 100 mg per kilogram bodyweight per day and most preferably in the range 5 to 20 mg per kilogram bodyweight per day; an optimum dose is about 10 mg per kilogram bodyweight per day. (Unless otherwise indicated, all weights of active ingredient are calculated as the parent compound of formula (I): for salts thereof the Figures would be increased proportionately.) The desired dose is preferably presented as two, three, four or more sub-doses administered at appropriate intervals throughout the day. These sub-doses may be administered in unit dosage forms, for example, containing 10 to 1000 mg, preferably 20 to 500 mg and most preferably 100 to 400 mg of active ingredient per unit dosage form.

While it is possible for the active ingredients to be administered alone it is preferable to present them as pharmaceutical formulations. The formulations, both for veterinary and for human use, of the present invention comprise at least one active ingredient, as above defined, together with one or more acceptable carriers therefor and optionally other therapeutic ingredients. The carrier(s) must be "acceptable" in the sense of being compatible with the other ingredients of the formulation and not deleterious to the recipient thereof.

The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as a oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

For infections of the eye or other external tissues for example mouth and skin, the formulations are preferably applied as a topical ointment or cream containing the active ingredient in an amount of, for example, 0.075 to 20% w/w, preferably 0.2 to 15% w/w and most preferably 0.5 to 10% w/w. When formulated in an ointment, the active ingredients may be employed with either paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol and mixtures thereof. The topical formulations may desirably include a compound which enhances absorption or penetration of the active ingredient through the skin or other affected areas. Examples of such dermal penetration enhancers include dimethylsulphoxide and related analogues.

Formulations suitable for topical administration to the eye also include eye drops wherein the active ingredient is dissolved or suspended in a suitable carrier, especially in aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavoured basis, usually sucrose and acacia or tragacanth; pastilles comprising the active ingredient in an inert basis such as gelatin and glycerine, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for nasal administration wherein the carrier is a solid include a coarse powder having a particle size for example in the range 20 to 500 microns which is administered in the manner in which snuff is taken, i.e. by rapid inhalation through the nasal passage from a container of powder held close up to the nose. Suitable formulations wherein the carrier is a liquid, for administration as for example a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described. Formulations for intramuscular administration are particularly preferred.

Preferred unit dosage formulations are those containing a daily dose or daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavouring agents.

The present invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

For oral administration the compositions can be in the form of a tablet, granule drench, paste, cachet, capsule or feed supplement. Granules may be made by the well known techniques of wet granulation, precompression or slugging. They can be administered to animals in an inert liquid vehicle so as to form a drench, or in a suspension with water or oil base. Preferably further accessory ingredients such as a dispensing agent are included. These formulations preferably contain from 15 to 85% of the active ingredient.

The following Examples are for exemplification purposes only and should not be limiting of the invention.

EXAMPLE A

Preparation of 9-(2-Valeryloxyethoxymethyl) guanine

A mixture of acyclovir prepared according to UK Patent No. 1523865 (3.11 moles), 4-dimethylaminopyridine (4.91 moles) and dimethylformamide (5.6 L) was stirred under nitrogen with heating on steam bath to give a homogeneous solution. On cooling to room temperature valeryl chloride (4.91 moles) was added dropwise while the temperature was maintained at 20°–25° C. Progress of the reaction was monitored by HPLC (Partisil ODS-3, methanol:water 50:50) and the reaction was terminated when the level of residual acyclovir was less than 0.5% (AUC). The mixture was cooled to 5° C., filtered and the cake was washed with dimethylformamide (200 ml). The combined filtrates were diluted with absolute ethanol (1 L), stirred for two hours at ambient temperature and concentrated to a thick oil. Methanol (16 L) was added and the resulting suspension was refluxed for 1.5 hours, cooled to 5° C. and filtered. The crude product was washed with methanol (200 mL) and dried under vacuum to constant weight to give 819 g (85.1% yield) of 9-(2-valeryloxyethoxymethyl) guanine, M.p. 215°–217° C.

Crude 9-(2-valeryloxyethoxymethyl) guanine (1994 g) was dissolved in refluxing methanol (12.5 L) over 3 hours. The hazy solution was cooled to ambient temperature, filtered and the cake was washed with methanol (1.5 L). Drying under vacuum to constant weight provided 1912 g (95.9% recovery) of the title compound as a white powder: M.p 223°–224° C.; TLC, R. 0.68 (selica gel, chloroform:methanol 7:3).

Anal. Calcd for $C_{13}H_{19}N_5$: C. 50.48; H, 6.19; N. 22.64 Found: C, 50.56, H, 6.13: N, 22.61.

'H-NMR (DMSO-$d_6$) $\delta$10.63 (s, 1.3 NHCO); 7.82 (s, 1, C-8); 6.52 (s, 2, $NH_2$); 5.35 (s, 2, N-$CH_2$O); 4.09 (t, 2, $CH_2CH_2OCO$); 3.66 (t, 2, $CH_2CH_2O$; 2.22 (t, 2, $CH_2$); 1.44 (m, 2, $CH_2$); 1.24 (m, 2, $CH_2$); 0.84 (t, 3, $CH_3$).

EXAMPLE 1: OPHTHALMIC SOLUTION

| | |
|---|---|
| Active ingredient | 0.5 |
| Sodium chloride, analytical grade | 0.9 g |
| Thiomersal | 0.001 g |
| Purified water to | 100 ml |
| pH adjusted to | 7.5 |

EXAMPLE 2: TABLET FORMULATIONS

The following formulations A, B and C are prepared by wet granulation of the ingredients with a solution of povidone, followed by addition of magnesium stearate and compression.

| | mg/tablet | mg/tablet |
|---|---|---|
| Formulation A | | |
| Active ingredient | 250 | 250 |
| Lactose B.P. | 210 | 26 |
| Povidone B.P. | 15 | 9 |
| Sodium Starch Glycollate | 20 | 12 |
| Magnesium Stearate | 5 | 3 |
| | 500 | 300 |
| Formulation B | | |
| Active ingredient | 250 | 250 |
| Lactose | 150 | — |
| Avicel PH 101 | 60 | 26 |
| Povidone B.P. | 15 | 9 |
| Sodium Starch Glycollate | 20 | 12 |
| Magnesium Stearate | 5 | 5 |
| | 500 | 300 |
| Formulation C | | |
| Active ingredient | 100 | |
| Lactose | 200 | |
| Starch | 50 | |
| Povidone B.P. | 5 | |
| Magnesium stearate | 4 | |
| | 359 | |

The following formulations, D and E, are prepared by direct compression of teh admixed ingredients. The lactose used in Formulation E is of the direct compression type.

| | mg/tablet |
|---|---|
| Formulation D | |
| Active Ingredient | 250 |
| Pregelatinised Starch NF15 | 150 |
| | 400 |
| Formulation E | |
| Active Ingredient | 250 |
| Lactose | 150 |
| Avicel | 100 |
| | 500 |

Formulation F (Controlled Release Formulation)

The formulation is prepared by wet granulation of the ingredients (below) with a solution of povidone followed by the addition of magnesium stearate and compression.

| | mg/tablet |
|---|---|
| Active Ingredient | 500 |
| Hydroxypropylmethylcellulose (Methocel K4M Premium) | 112 |
| Lactose B.P. | 53 |
| Povidone B.P.C. | 28 |
| Magnesium Stearate | 7 |
| | 700 |

Drug release takes place over a period of about 6–8 hours and was complete after 12 hours.

EXAMPLE 3: CAPSULE FORMULATIONS

Formulation A

A capsule formulation is prepared by admixing the ingredients of Formulation D in Example C above and filling into a two-part hard gelatin capsule. Formulation B (infra) is prepared in a similar manner.

|  | mg/capsule |
|---|---|
| Formulation B | |
| Active Ingredient | 250 |
| Lactose B.P. | 143 |
| Sodium Starch Glycollate | 25 |
| Magnesium Stearate | 2 |
|  | 420 |
| Formulation C | |
| Active Ingredient | 250 |
| Macrogol 4000 BP | 350 |
|  | 600 |

Capsules are prepared by melting the Macrogol 4000 BP, dispersing the active ingredient in the melt and filling the melt into a two-part hard gelatin capsule.

| Formulation D | mg/capsule |
|---|---|
| Active Ingredient | 250 |
| Lecithin | 100 |
| Arcachis Oil | 100 |
|  | 450 |

Capsules are prepared by dispersing the active ingredient in the lecithin and arachis oil and filling the dispersion into soft, elastic gelating capsules.

Formulation E (Controlled Release Capsule)

The following controlled release capsule formulation is prepared by extruding ingredients a, b, and c using an extruder, followed by spheronisation of the extrudate and drying. The dried pellets are then coated with release-controlling membrane (d) and filled into a two-piece, hard gelatin capsule.

|  | mg/capsule |
|---|---|
| (a) Active Ingredient | 250 |
| (b) Microcrystalline Cellulose | 125 |
| (c) Lactose BP | 125 |
| (d) Ethyl Cellulose | 13 |
|  | 513 |

EXAMPLE 4: INJECTABLE FORMULATION

| Active Ingredient | 0.200 g |
|---|---|
| Sterile, pyrogen free phosphate buffer (pH 7.0) to | 10 ml |

The active ingredient is dissolved in most of the phosphate buffer (35°–40° C.), then made up to volume and filtered through a sterile micropore filter into a sterile 10 ml amber glass vial (type 1) and sealed with sterile closures and overseals.

EXAMPLE 5 INTRAMUSCULAR INJECTION

| Active Ingredient | 0.20 g |
|---|---|
| Benzyl Alcohol | 0.10 g |
| Glycofurol 75 | 1.45 g |
| Water for Injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml glass vials (type 1).

EXAMPLE 6 SYRUP SUSPENSION

| Active Ingredient | 0.2500 g |
|---|---|
| Sorbitol Solution | 1.5000 g |
| Glycerol | 2.000 g |
| Dispersible Cellulose | 0.0750 g |
| Sodium Benzoate | 0.0050 g |
| Flavour, Peach 17.42.3169 | 0.0125 ml |
| Purified Water q.s. to | 5.0000 ml |

The sodium benzoate is dissolved in a portion of the purified water and the sorbitol solution added. The active ingredient is added and dispersed. In the glycerol is dispersed the thickener (dispersible cellulose). The two dispersions are mixed and made up to the required volume with the purified water. Further thickening is achieved as required by extra shearing of the suspension.

EXAMPLE 7 SUPPOSITORY

|  | mg/suppository |
|---|---|
| Active Ingredient (63 μm)* | 250 |
| Hard Fat, BP (Witepsol H15 - Dynamit NoBel) | 1770 |
|  | 2020 |

One-fifth of the Witepsol H15 is melted in a steam-jacketed pan at 45° C. maximum. The active ingredient is sifted through a 200 μm sieve and added to the molten base with mixing, using a silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250 μm stainless steel screen and, with continuous stirring, is allowed to cool to 40° C. At a temperature of 38° C. to 40° C. 2.02 g of the mixture is filled into suitable plastic moulds. The suppositories are allowed to cool to room temperature.

EXAMPLE 8: PESSARIES

|  | mg/pessary |
|---|---|
| Active Ingredient 63 μm | 250 |
| Anhydrate Dextrose | 380 |
| Potato Starch | 363 |
| Magnesium Stearate | 7 |
|  | 1000 |

The above ingredients are mixed directly and pessaries prepared by direct compression of the resulting mixture.

EXAMPLE 9

Eye Drop Formulation

An eye drop formulation is prepared by dissolving the compound according to the invention in a concentration of 1% (weight/vol) in an isotonic buffer solution which contains 1.52 g boric acid, 0.0008 g borax and 0.01 g benzalkonium chloride per 100 ml distilled water. The pH of the solution is 5.7.

Antiviral Activity

Herpes Simplex Virus (HSV 1) was assayed in monolayers of Vero cells in multiwell trays. Activity of compounds was determined in the plaque reduction assay, in which a cell monolayer was infected with a suspension of HSV 1, and then overlaid with nutrient agarose in the form of a gel to ensure that there was no spread of virus throughout the culture. A range of concentrations of compound of known molarity was incorporated in the nutrient agarose overlay. Plaque numbers at each concentration are expressed as percentages of the control and a dose-response curve was drawn. From this curve the 50% inhibitory concentration ($IC_{50}$) was estimated.

Compound: $IC_{50}$ μM
Example A: 0.2 μm
Acyclovir: ~0.1 μM

Determination of Oral Bioavailability

Long Evans Rates are administered the compound to be tested by gavage at a dose equivalent to 25 mg/kg acyclovir. The urine is collected for 24 and 48 hours post-dose, ultrafiltered, and analysed by reverse-phase high-pressure liquid chromatography. The oral bioavailability of the compound is expressed as the percent of the dose excreted in the urine as acyclovir.

| Compound | Urinary Recovery (% of dose) as acyclovir |
|---|---|
| Example A | 34 |
| Acyclovir (ACV) | 15 |

I claim:
1. 9-(2-valeryloxyethoxymethyl)guanine.
2. A pharmacologically acceptable salt of 9-(2-valeryloxyethoxymethyl)guanine.
3. A pharmaceutical composition comprising an effective antiviral treatment amount of 9-(2-valeryloxyethoxymethyl)guanine or a pharmacologically acceptable salt thereof together with a pharmaceutically acceptable carrier therefore.
4. A tablet or capsule containing an effective antiviral treatment amount of 9-(2-valeryloxyethoxymethyl)guanine or a pharmacologically acceptable salt thereof together with a pharmaceutically acceptable carrier therefore.
5. A method of generating acyclovir in a mammal which comprises internally administering to said mammal the compound 9-(2-valeryloxyethoxymethyl)guanine or a pharmacologically acceptable salt thereof.
6. A method of treating a herpes virus infection in a mammal which comprises administering to said mammal an effective herpes virus infection treatment amount of 9-(2-valeryloxyethoxymethyl)guanine or a pharmacologically acceptable salt thereof.
7. The method of claim 6, in which the infection is a herpes simplex, varicella or zoster infection.

* * * * *